(12) United States Patent
Nie et al.

(10) Patent No.: US 9,896,498 B2
(45) Date of Patent: Feb. 20, 2018

(54) TUMOR VASCULAR DISRUPTING AGENT POLYPEPTIDE, GENE, EXPRESSION VECTOR, AND USE THEREOF

(71) Applicant: Beijing Hua'an Innovation Biotechnology Co., Ltd., Beijing (CN)

(72) Inventors: Guangjun Nie, Beijing (CN); Suping Li, Beijing (CN); Yanhua Tian, Beijing (CN); Ying Zhao, Beijing (CN)

(73) Assignee: Beijing Hua'an Innovation Biotechnology Co., Ltd., Beijing (CN)

( * ) Notice: Subject to any disclaimer, the term of this patent is extended or adjusted under 35 U.S.C. 154(b) by 0 days.

(21) Appl. No.: 15/324,669

(22) PCT Filed: Sep. 8, 2015

(86) PCT No.: PCT/CN2015/089116
§ 371 (c)(1),
(2) Date: Jun. 2, 2017

(87) PCT Pub. No.: WO2016/004906
PCT Pub. Date: Jan. 14, 2016

(65) Prior Publication Data
US 2017/0267741 A1 Sep. 21, 2017

(30) Foreign Application Priority Data
Jul. 8, 2014 (CN) .......................... 2014 1 0323457

(51) Int. Cl.
*C07K 14/70* (2006.01)
*C07K 14/705* (2006.01)
*A61K 38/00* (2006.01)

(52) U.S. Cl.
CPC ........ *C07K 14/70596* (2013.01); *A61K 38/00* (2013.01); *C07K 2319/01* (2013.01)

(58) Field of Classification Search
None
See application file for complete search history.

(56) References Cited

FOREIGN PATENT DOCUMENTS

| CN | 102153653 A | * | 8/2011 |
| CN | 103705465 A | * | 4/2014 |
| CN | 104045717 B | * | 7/2016 |

OTHER PUBLICATIONS

International Search Report and Written Opinion of the International Search Authority for PCT/CN2015/089116, dated Dec. 4, 2015, 14 pages.
International Preliminary Report on Patentability Chapter II for PCT/CN2015/089116, completed Nov. 7, 2016, 14 pages.
First Examination Report in CN 201410323457.6, dated Nov. 4, 2015, 9 pages.
Notice of Allowance in CN 201410323457.6, dated May 26, 2016, 5 pages.

* cited by examiner

*Primary Examiner* — Maury Audet
(74) *Attorney, Agent, or Firm* — Morrison & Foerster LLP

(57) ABSTRACT

The present invention relates to a tumor vascular disrupting agent polypeptide, gene, expression vector, and use thereof. The tumor vascular disrupting agent polypeptide has the amino acid sequence as shown by SEQ ID NO: 1. The polypeptide comprises a truncated tissue factor (tTF) and a tumor-targeting molecule (pHLIP); the factor and the molecule are connected by 5 amino acids, thereby ensuring the function of each not being affected by the other; the fusion protein can be positioned to the surface of a tumor vascular endothelial cell by means of the pHLIP, and provides the blood coagulation feature of the tTF in a tumor vessel and forms a thrombus, thereby disrupting the blood supply to the tumor area and treating tumor. The polypeptide of the present invention is significant to the treatment of tumor, and can be used in medicines for treating tumors.

13 Claims, 1 Drawing Sheet

SEQUENCE LISTING

<160> NUMBER OF SEQ ID NOS: 5

<210> SEQ ID NO 1
<211> LENGTH: 259
<212> TYPE: PRT
<213> ORGANISM: artificial sequence
<220> FEATURE:
<223> OTHER INFORMATION: synthetic construct
<220> FEATURE:
<223> OTHER INFORMATION: TUMOR VASCULAR DISRUPTING AGENT POLYPEPTIDE

<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Gly Gly Gly Gly Ser
    210                 215                 220

Ala Glu Gln Asn Pro Ile Tyr Trp Ala Arg Tyr Ala Asp Trp Leu Phe
225                 230                 235                 240

Thr Thr Pro Leu Leu Leu Leu Asp Leu Ala Leu Leu Val Asp Ala Asp
                245                 250                 255

Glu Gly Thr

<210> SEQ ID NO 2
<211> LENGTH: 219
<212> TYPE: PRT
<213> ORGANISM: artificial sequence
<220> FEATURE:
<223> OTHER INFORMATION: synthetic construct
<220> FEATURE:
<223> OTHER INFORMATION: amino acid sequence of tTF

```
<400> SEQUENCE: 2

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 3
<211> LENGTH: 5
<212> TYPE: PRT
<213> ORGANISM: artificial sequence
<220> FEATURE:
<223> OTHER INFORMATION: synthetic construct
<220> FEATURE:
<223> OTHER INFORMATION: domain of linkage

<400> SEQUENCE: 3

Gly Gly Gly Gly Ser
1               5

<210> SEQ ID NO 4
<211> LENGTH: 35
<212> TYPE: PRT
<213> ORGANISM: artificial sequence
<220> FEATURE:
<223> OTHER INFORMATION: synthetic construct
<220> FEATURE:
<223> OTHER INFORMATION: domain of linkage

<400> SEQUENCE: 4

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35
```

```
<210> SEQ ID NO 5
<211> LENGTH: 777
<212> TYPE: DNA
<213> ORGANISM: artificial sequence
<220> FEATURE:
<223> OTHER INFORMATION: synthetic construct
<220> FEATURE:
<223> OTHER INFORMATION: Gene of TUMOR VASCULAR DISRUPTING AGENT

<400> SEQUENCE: 5
tcaggcacta caaatactgt ggcagcatat aatttaactt ggaaatcaac taatttcaag     60
acaattttgg agtgggaacc caaacccgtc aatcaagtct acactgttca aataagcact    120
aagtcaggag attggaaaag caaatgcttt tacacaacag acacagagtg tgacctcacc    180
gacgagattg tgaaggatgt gaagcagacg tacttggcac gggtcttctc ctacccggca    240
gggaatgtgg agagcaccgg ttctgctggg gagcctctgt atgagaactc cccagagttc    300
acaccttacc tggagacaaa cctcggacag ccaacaattc agagttttga acaggtggga    360
acaaaagtga atgtgaccgt agaagatgaa cggactttag tcagaaggaa caacactttc    420
ctaagcctcc gggatgtttt tggcaaggac ttaatttata cactttatta ttggaaatct    480
tcaagttcag gaaagaaaac agccaaaaca aacactaatg agttttttgat tgatgtggat    540 aaaggagaaa actactgttt cagtgttcaa gcagtgattc cctcccgaac agttaaccgg    600
aagagtacag acagcccggt agagtgtatg ggccaggaga aaggggaatt cagagaaggt    660
ggtggtggtt ctgctgaaca gaacccgatc tactgggctc gttacgctga ctggctgttc    720
accaccccgc tgctgctgct ggacctggct ctgctggttg acgctgacga aggtacc      777
```

TUMOR VASCULAR DISRUPTING AGENT POLYPEPTIDE, GENE, EXPRESSION VECTOR, AND USE THEREOF

CROSS-REFERENCE TO RELATED APPLICATIONS

This application is a U.S. National Phase of International Patent Application No. PCT/CN2015/089116, filed Sep. 8, 2015, which claims the benefit of Chinese Patent Application No. 201410323457.6, filed Jul. 8, 2014, each of which is hereby incorporated by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717412001400_SeqList.txt, date recorded: 6 Jan. 2017, size: 6,630 bytes).

TECHNICAL FIELD

The invention relates to technical field of the medicine for tumor treatment, particularly to a tumor blood vessel blocker polypeptide, gene, expression vector and their use thereof.

BACKGROUND OF THE INVENTION

The tumor blood vessel is the passage for tumor cells to obtain nutritional substances and remove metabolites as well as one of the key ways for tumor cells to escape and transfer, and its morphology and function are different from those of the normal blood vessel system of organism, thus, it is one of the key targets for tumor targeted therapy. The targeted therapy of tumor blood vessel mainly includes two modes of inhibiting generation of new-born blood vessels and blocking the existing tumor blood vessels, wherein the therapy of blocking the existing blood vessel treats the tumor by selectively damaging the existing tumor blood vessels, cutting off tumor blood supplying and inducing the tumor cell to generate ischemic necrosis. Therefore, how to specifically block the blood vessel of the tumor part without influencing the normal tissue blood vessel of organism becomes the hotspot of study.

Tissue factor (TF) is a transmembrane glycoprotein with molecular weight about 47 kDa, and it plays an important role for thrombopoiesis. Normally, TF is in the adventitial cells of vascular wall but not in circulation or doesn't contact the circulation blood. When the completeness of vascular wall is damaged, TF is exposed in the circulation blood, and activates coagulation cascade activation to display the hemostatic effect. TF consists of 263 amino acid residues, wherein 219 amino acid residues of the amino terminal are outside the cell membrane which is the active part of TF. It's proven by study that, when this part is in the free state, no coagulation activity exists, but when this part is anchored on the cell membrane and exposed in blood, the coagulation activity similar as the full-length factor generates, thus, the sequence of this part is called as the truncated tissue factor (tTF). In view of this characteristic, if molecule having tumor targeting function specially anchors tTF in tumor tissue, thrombopoiesis will be arisen in tumor blood specially, so as to cut off tumor blood supplying and metabolite removing pathway, accordingly to achieve the goal of treating tumor.

Tumor targeted molecule pHLIP is a polypeptide consisting of 35 amino acids. When circulating in body (pH=7.35-7.45), the tumor targeted molecule pHLIP is in the free extension state, but cannot be anchored in the specific tissue. When it reaches the tumor part (pH<7), the conformational change of acid response is generated to form α-helix structure, and the interactive action with cell membrane is also generated, then, the tumor targeted molecule pHLIP is inserted into cell membrane to be anchored in endothelial cell surface.

If above truncated tissue factor tTF and the tumor targeting molecule pHLIP are recombined into the fusion protein so as to ensure their respective functions not be influenced by each other. The fusion protein can be positioned to surface of endothelial cells of the tumor blood vessel by pHLIP, and display the coagulation function of tTF in the tumor blood vessel to generate thrombus, so as to block the blood supply for the tumor part and to achieve the goal of treating tumor, which has important significance for tumor treatment.

SUMMARY OF THE INVENTION

The invention discloses a tumor blood vessel blocker polypeptide, gene, expression vector and their use for preparing the medicine for tumor treatment. Said polypeptide is a fusion protein of recombination of above tTF and the tumor targeted molecule pHLIP with 5 amino acids linked between them to ensure their respective functions not influence by each other. Said fusion protein can locate on endothelial cell surface of tumor blood through tTF, and play coagulation function of tTF in tumor blood to form thrombus, thereby to cut off tumor blood supplying, accordingly to achieve the goal of treating tumor.

To meet the target, the invention adopts the following technical scheme:

In the first aspect, the invention provides a tumor blood vessel blocker polypeptide, said polypeptide has the amino acid sequence shown by SEQ ID NO: 1;

The amino acid sequence shown by SEQ ID NO: 1 is as follows:

```
                                          (SEQ ID NO: 1)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFREGGGGSAEQNPIYWARYADWLFTTPLL

LLDLALLVDADEGT.
```

The tumor blood vessel blocker polypeptide comprises an active domain, a connection domain and a targeting domain, which respectively display different functions.

The active domain consists of 219 amino acids with the following sequence:

```
                                          (SEQ ID NO: 2)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP
```

-continued

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

The sequence of the active domain is same as that of the amino acid residue sequence of tissue factor which is outside cell membrane. It doesn't have coagulation activity when it's in the free state. When positioned on the endothelial cell membrane of the tumor blood vessel by the targeting peptide, it can display function of tissue factor, activate coagulation way and induce thrombopoiesis. The connection domain consists of 5 amino acids with the sequence of GGGGS (SEQ ID NO: 3), which can ensure to keep complete functions of the active domain and the targeting domain of the fusion protein obtained by expression.

The targeting domain consists of 35 amino acids with the sequence of AEQNPIYWARYADWLFTTPLLLLDLALL-VDADEGT (SEQ ID NO: 4). The sequence of the targeting domain can generate the conformational change in subacidity environment of tumor part to form the α-helix structure and penetrate cell membrane so as to locate on the tumor blood vessel endothelial cell membrane.

The tumor blood vessel blocker polypeptide can response to subacidity feature of tumor and generate the conformational change to locate on endothelial cell of the tumor blood vessel and activate coagulation activity of the activity domain, so as to specifically form thrombosis in the tumor blood vessel and achieve the therapy goal of inhibiting tumor growth. However, in the normal physiological pH environment, the targeting domain cannot form the α-helix structure without membrane penetration function, thus, the activity domain cannot be located on cells and cannot play coagulation activity, in order to ensure no thrombosis is formed in blood vessels of normal parts when the medicine molecules circulate in the body, without any side effect caused. In addition, the tumor blood vessel blocker polypeptide doesn't need to be permeated into tumor tissue and can directly display the effect at the tumor blood vessel part, thus, dosage decreases, and it's not easy to generate drug resistance. Main part of the polypeptide comes from extracellular region of the personal tissue factor, thus, its immunogenicity is little, and it can reduce that the medicine is cleared by immunity during circulation in the body.

In this invention, compared with other tumor targeted peptide mediating tissue factors, which have been reported, the tumor blood vessel blocker polypeptide is closer to the natural conformation of tissue factor and consequently its coagulation activity is better.

In second aspect: the invention provides a tumor blood vessel blocker gene, said gene has nucleotide sequence which encodes said tumor blood vessel blocker polypeptide.

A person skilled in the art shall understand that, because of codon degeneracy, the nucleotide sequence encoding the tumor blood vessel blocker polypeptide of the invention is not unique, all of the nucleotide sequences which can encode and express the tumor blood vessel blocker polypeptide can be believed as the tumor blood vessel blocker gene of the invention.

However, the invention particularly provides a tumor blood vessel blocker gene which comprises the nucleotide sequence shown by SEQ ID NO:5.

Wherein, the nucleotide sequence shown by SEQ ID NO: 5 is as follows:

(SEQ ID NO: 5)
TCAGGCACTACAAATACTGTGGCAGCATATAATTTAACTTGGAAATCA

ACTAATTTCAAGACAATTTTGGAGTGGGAACCCAAACCCGTCAATCAA

GTCTACACTGTTCAAATAAGCACTAAGTCAGGAGATTGGAAAAGCAAA

TGCTTTTACACAACAGACACAGAGTGTGACCTCACCGACGAGATTGTG

AAGGATGTGAAGCAGACGTACTTGGCACGGGTCTTCTCCTACCCGGCA

GGGAATGTGGAGAGCACCGGTTCTGCTGGGGAGCCTCTGTATGAGAAC

TCCCCAGAGTTCACACCTTACCTGGAGACAAACCTCGGACAGCCAACA

ATTCAGAGTTTTGAACAGGTGGGAACAAAAGTGAATGTGACCGTAGAA

GATGAACGGACTTTAGTCAGAAGGAACAACACTTTCCTAAGCCTCCGG

GATGTTTTTGGCAAGGACTTAATTTATACACTTTATTATTGGAAATCT

TCAAGTTCAGGAAAGAAAACAGCCAAAACAAACACTAATGAGTTTTTG

ATTGATGTGGATAAAGGAGAAAACTACTGTTTCAGTGTTCAAGCAGTG

ATTCCCTCCCGAACAGTTAACCGGAAGAGTACAGACAGCCCGGTAGAG

TGTATGGGCCAGGAGAAAGGGGAATTCAGAGAAGGTGGTGGTGGTTCT

GCTGAACAGAACCCGATCTACTGGGCTCGTTACGCTGACTGGCTGTTC

ACCACCCCGCTGCTGCTGCTGGACCTGGCTCTGCTGGTTGACGCTGAC

GAAGGTACC.

In third aspect: the invention provides an expression vector of tumor blood vessel blocker, said expression vector comprises the nucleotide sequence encoding the tumor blood vessel blocker polypeptide.

A person skilled in the art shall understand that, because of codon degeneracy, the nucleotide sequence encoding the tumor blood vessel blocker polypeptide of the invention is not unique, all of the nucleotide sequences which can encode and express the tumor blood vessel blocker polypeptide can be believed as the tumor blood vessel blocker gene of the invention, thus, any expression vector encoding and expressing the tumor blood vessel blocker polypeptide shall be understood as the protection scope of the invention.

However, the invention specially provides an expression vector which includes the nucleotide sequence shown by the above SEQ ID NO: 5.

A person skilled in the art shall understand that, in this invention, the vector plasmid used for the expression vector is not specially limited, since on the basis of knowing the gene sequence of the invention and combining with common general knowledge in this art, the person skilled in the art can select a proper vector plasmid for the gene expression of the invention.

However, the invention specially provides a vector plasmid, which is a common vector plasmid of pET30a. Thus, the expression vector of the invention preferably adopts the expression vector constructed by pET30a vector plasmid.

In the fourth aspect, the invention provides the use of the tumor blood vessel blocker polypeptide in preparing medicine for tumor treatment.

In the invention, the tumor blood vessel blocker polypeptide can be obtained by the following steps: designing the corresponding gene sequence, constructing the expression plasmid of the fusion protein, transferring it into BL21 *E. coli.*, and then using IPTG for inducing expression and purification to obtain the tumor blood vessel blocker with tumor targeting property and coagulation activity.

The invention has the following advantages:

(1) The main part of the tumor blood vessel blocker comes from the self-sourced tissue factor extracellular region, thus, immunogenicity is little, and it can excellently avoid clearance of immune system.

(2) The tumor blood vessel blocker skillfully employs an acid-responsive tumor targeting peptide to locate the tissue factor on the tumor blood vessel endothelial cells. Compared with the other methods of ligand-receptor positioning tissue factors, the tumor blood vessel blocker polypeptide of the invention is closer to the natural conformation of the tissue factor and has better coagulation activity.

(3) The invention can be employed in the other hemorrhagic diseases by changing the targeting molecule, thus, this invention has a wide application prospect.

EMBODIMENTS

The following describes the implementation plan of the invention in detail by combining with embodiments. A person skilled in the art shall understand that, the following examples are only the preferable embodiments of the invention, it's only for better understanding the invention but shall not be deemed as to limit the scope of the invention.

All experiment methods used in the following embodiments are conventional methods, unless other specified; and all experiment materials are purchased from the conventional biochemical reagent manufacturers unless other specified.

Example 1: Construction of Fusion Protein Expression Vector

Firstly, the gene sequence of tissue factor extracellular 219 amino acids (shown as SEQ ID NO:2) is found by searching from NCBI website, and secondly, the amino acid sequences of the tumor targeting peptide (shown as SEQ ID NO:3) and the connection part are translated to get the gene sequence, to get the gene sequence of the fusion protein shown by SEQ ID NO: 5. Gene of the fusion protein is synthesized by the full-gene synthesis method, and restriction enzyme cutting sites Nde I and Xho I are respectively designed at both ends of the gene, and then, the fusion protein gene is connected into the pET30a vector through the above restriction enzyme cutting sites so as to get the fusion protein expression vector.

Example 2: Expression and Purification of Fusion Protein (1) Expression of Fusion Protein The above expression vector of fusion protein is transformed into BL21 *E. coli.*; firstly, 5 µL of bacterial fluid was inoculated into 5 mL of LB liquid nutrient medium, and incubated by shake cultivation for 16 h at 37° C., 200×rpm. The cultivated bacterial fluid was innoculated into 500 mL of LB liquid nutrient medium, and incubated by shake cultivation for 16 h at 37° C., 200×rpm, to 0D=0.6~0.8, and then induced expression is conducted for 4 h by using IPTG (0.5 mM).

(2) Purification of Fusion Protein

Above IPTG induced-expressed bacterial fluid was centrifuged (6000×rpm, 5 min); the liquid supernatant was discarded, and the bacteria was collected. precipitate was, blown off with the 25 mL 10 mM Tris-HCl (pH=8.0) solution; the bacteria were broken with ultrasound, and centrifuged for 10 min at 12000×rpm with liquid supernatant removed; the precipitate obtained by ultrasonic centrifugation was re-suspended with 25 mL of 10 mM Tris-HCl (pH=8.0) solution, and placed for 10 min. Above operation was repeated for one time again and get the precipitate. The precipitate was re-suspended by adding little amount of 10 mM Tris-HCl (pH=8.0) solution, and then 8 mL of 10 mM Tris-HCl (pH=8.0) solution containing 8M carbamide was added to dissolve the protein, and was centrifuged for 10 min at 12000×rpm, and then to collect the liquid supernatant.

Figure 1:
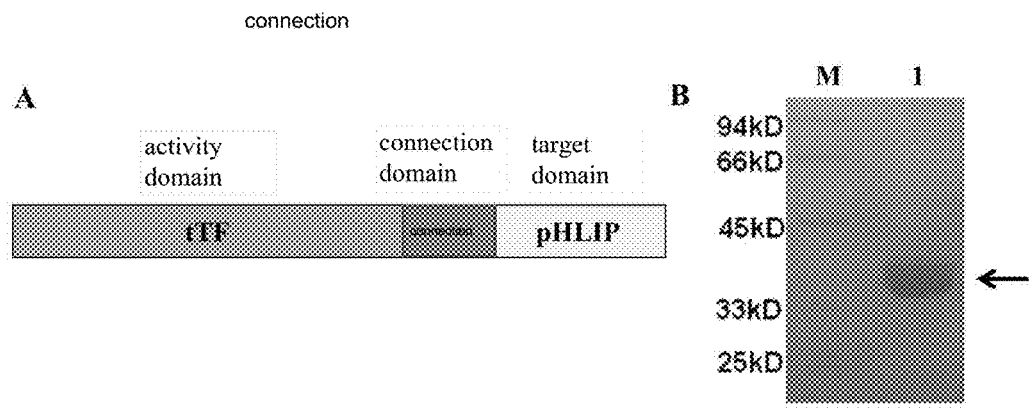
FIG. 1 is the structural diagram (A) of the tumor blood vessel blocker polypeptide (fusion protein) of this invention and identification results of SDS-PAGE electrophoresis (B) of the fusion protein. Wherein, the tumor blood vessel blocker polypeptide comprises three domains: an activity domain, a connection domain and a target domain; M means protein standard molecular weight; 1 means lane of the fusion protein, and location pointed out by arrow is the fusion protein.

The fusion protein was identified with SDS-PAGE electrophoresis, with results shown as FIG. 1 (B); clear and pure bands which are higher than 30 KDa can be seen, which is consistent with expectation.

Example 3: Effect Experiments of Tumor Blood Vessel Blocker

Figure 2:
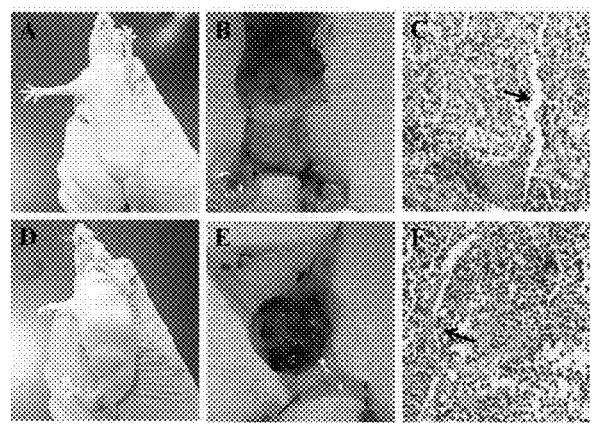
FIG. 2 shows the therapy effects of 12 hours after injecting tumor blood vessel blocker of the invention into the mammary cancer tumor model of nude mice through tail vein, wherein, (A) is the in-vitro morphology of the tumor-bearing mice which is injected with physiological saline (control), (B) is the control tumor, (C) is the control tumor pathological section (the arrow means the tumor blood vessel without thrombopoiesis), (D) is the in-vitro morphology of the tumor-bearing mice which is injected with tumor blood vessel blocker, (E) is the tumor after injecting tumor blood vessel blocker, and (F) is the tumor pathological section after injecting tumor blood vessel blocker (the arrow directs to the tumor blood vessel with clear thrombopoiesis).

The tumor blood vessel blocker polypeptide provided by embodiment 2 is injected into the mammary cancer tumor model of nude mice by the tail vein, according to the amount of 833 ug/kg body weight or 20 ug/per mouse; the therapy effects were observed after 12 hours and mice injecting physiological saline were taken as the control group. The results are shown as FIG. 2.

Compared with the tumor-bearing mice (A) injecting the physiological saline, the tumor blood vessel blocker of the invention can cause the tumor part to turn on the deep red (D) which can be observed by naked eyes; and after dissection, the normal flesh pink can be observed in the tumor (B) of the control group while the tumor injecting the tumor blood vessel blocker (E) appears the dark red which is clearly caused by thrombus; it's shown by tumor pathological sections that, compared with the control group (C), and the group (F) injecting the tumor blood vessel blocker forms clear thrombus (indicated by the arrow) in the tumor blood vessel.

The applicants hereby declare that, the invention explains the detailed features and detailed methods through above embodiments, but the invention is not limited by above detailed features and detailed methods, i.e., it does not mean that, it's necessary to implement the invention only by depending on above detailed features and detailed methods. A person skilled in the art shall understand that, any improvement of the invention, equivalent substitution of components used by the invention and adding of auxiliary components, selection of detailed ways, etc., are all in the protection scope and disclosure scope of the invention.

---

The invention claimed is:

1. A tumor blood vessel blocker polypeptide, from its amino terminal to carboxyl terminal, comprising:
   a truncated tissue factor (tTF) sequence comprising the amino acid sequence set forth in SEQ ID NO: 2,
   a connection domain comprising the amino acid sequence set forth in SEQ ID NO: 3, and
   a tumor targeting molecule pHLIP sequence comprising the amino acid sequence set forth in SEQ ID NO: 4.

2. A tumor blood vessel blocker polynucleotide which encodes the tumor blood vessel blocker polypeptide of claim 1.

3. The tumor blood vessel blocker polynucleotide of claim 2, comprising the polynucleotide sequence set forth in SEQ ID NO: 5.

4. An expression vector, comprising the tumor blood vessel blocker polynucleotide of claim 2.

5. The expression vector of claim 4, wherein said expression vector is constructed using a pET30a plasmid vector.

6. The expression vector of claim 4, comprising the polynucleotide sequence set forth in SEQ ID NO: 5.

7. The expression vector of claim 6, wherein said expression vector is constructed using a pET30a plasmid vector.

8. A composition, comprising the tumor blood vessel blocker polypeptide of claim 1.

9. A composition, comprising the tumor blood vessel blocker polynucleotide of claim 2.

10. A composition, comprising the expression vector of claim 4.

11. The composition of claim 10, wherein the expression vector comprises the polynucleotide sequence set forth in SEQ ID NO: 5.

12. A method of preparing the tumor blood vessel blocker polypeptide of claim 1, comprising:
   transferring the expression vector of claim 4 into an expression system, and
   inducing expression to obtain the tumor blood vessel blocker polypeptide.

13. The method of claim 12, wherein the expression vector comprises the polynucleotide sequence set forth in SEQ ID NO: 5.

* * * * *